United States Patent
Huder et al.

(10) Patent No.: US 10,874,983 B2
(45) Date of Patent: Dec. 29, 2020

(54) PROCESS AND APPARATUS FOR THE RECOVERY OF METHANOL

(71) Applicant: L'Air Liquide, Societe Anonyme pour l'Etude et l'Exploitation des Procedes Georges Claude, Paris (FR)

(72) Inventors: Karin Huder, Frankfurt am Main (DE); Veronika Gronemann, Karben (DE); Tobias Oelmann, Bad Vilbel (DE)

(73) Assignee: L'Air Liquide Societe Anonyme Pour L'Etude Et L'Exploitation Des Procedes Georges Claude, Paris (FR)

(*) Notice: Subject to any disclaimer, the term of this patent is extended or adjusted under 35 U.S.C. 154(b) by 387 days.

(21) Appl. No.: 16/063,500

(22) PCT Filed: Dec. 6, 2016

(86) PCT No.: PCT/EP2016/025169
§ 371 (c)(1),
(2) Date: Jun. 18, 2018

(87) PCT Pub. No.: WO2017/102094
PCT Pub. Date: Jun. 22, 2017

(65) Prior Publication Data
US 2020/0282358 A1    Sep. 10, 2020

(51) Int. Cl.
*B01D 53/74* (2006.01)
*C07C 29/76* (2006.01)
(Continued)

(52) U.S. Cl.
CPC .......... *B01D 53/74* (2013.01); *B01D 53/44* (2013.01); *C07C 29/151* (2013.01); *C07C 29/76* (2013.01); *B01J 19/0053* (2013.01)

(58) Field of Classification Search
CPC ........ B01D 53/74; B01D 53/44; C07C 29/76; C07C 29/151; B01J 19/0053
See application file for complete search history.

(56) References Cited

U.S. PATENT DOCUMENTS

| 4,326,041 A | 4/1982 | Bahnisch |
| 5,827,901 A | 10/1998 | Konig et al. |
| 6,258,860 B1 | 7/2001 | Weedon et al. |

FOREIGN PATENT DOCUMENTS

| DE | 2934332 A1 | 3/1981 |
| EP | 0009385 A1 | 4/1980 |

(Continued)

OTHER PUBLICATIONS

Joshi et al. ("Methanol Production Increase from Closed-Loop Selective Recovery of Process Vapor Effluents" from IP.com at:https://ip.com/IPCOM/000218671, Jun. 2012, 11 pages).*

(Continued)

*Primary Examiner* — Rosalynd A Keys
(74) *Attorney, Agent, or Firm* — Justin K. Murray

(57) ABSTRACT

There is proposed an efficient recovery of methanol from waste gases loaded with methanol in an integrated flow chart for the production and processing of methanol. The methanol fractions separated from the waste gases are recovered within the already existing, distillative processing of the crude methanol to pure methanol, so that no separate apparatuses are required for the recovery of the methanol from the loaded scrubber waste waters. The valuable substance methanol is recovered and the impact on the environment is reduced. By means of particular aspects of the invention the need for water as washing agent can be reduced further.

17 Claims, 4 Drawing Sheets

(51) Int. Cl.
*B01D 53/44* (2006.01)
*C07C 29/151* (2006.01)
*B01J 19/00* (2006.01)

(56) References Cited

FOREIGN PATENT DOCUMENTS

| EP | 0790226 A1 | 8/1997 |
| EP | 0802893 B1 | 10/1997 |
| EP | 1016643 B1 | 7/2000 |
| EP | 2168938 A1 | 3/2010 |
| JP | S5620528 A | 2/1981 |
| JP | S5655324 A | 5/1981 |
| JP | 2001039911 A | 2/2001 |

OTHER PUBLICATIONS

Ullmann's Encyclopedia of Industrial Chemistry, Chapter "Methanol", Sub-chapter 5.2 "Synthesis"; 2005, pp. 1-25; Wiley-VCH Verlag GmbH & Co. KGaA Weinheim.
Intl Search Report and Written Opinion for corresponding PCT/EP2016/025169, dated Apr. 4, 2017.

* cited by examiner

PROCESS AND APPARATUS FOR THE RECOVERY OF METHANOL

CROSS REFERENCE TO RELATED APPLICATIONS

This application is a § 371 of International PCT Application PCT/EP2016/025169, filed Dec. 6, 2016, which claims the benefit of EP15400057.4, filed Dec. 18, 2015, both of which are herein incorporated by reference in their entireties.

FIELD OF THE INVENTION

The present invention relates to a process for the recovery of methanol from process waste gases of the methanol synthesis. Furthermore, the invention comprises an apparatus for carrying out this process.

BACKGROUND OF THE INVENTION

Processes for the production of methanol by catalytic conversion of synthesis gas containing hydrogen and carbon oxides have long since been known to those skilled in the art. For example, in Ullmann's Encyclopedia of Industrial Chemistry, Sixth Edition, 1998 Electronic Release, Chapter "Methanol", Sub-chapter 5.2 "Synthesis", various basic processes for the production of methanol are described.

A more advanced, two-stage process for the production of methanol is known for example from EP 0 790 226 B1. The methanol is produced in a cyclic process in which a mixture of fresh and partly reacted synthesis gas first is supplied to a water-cooled reactor and then to a gas-cooled reactor, in each of which the synthesis gas is converted to methanol on a copper-based catalyst. The methanol produced in the process is separated from the synthesis gas to be recirculated, which as coolant is then countercurrently guided through the gas-cooled reactor and preheated to a temperature of 220 to 280° C., before it is introduced into the first synthesis reactor. A part of the synthesis gas to be recirculated is removed from the process as purge stream (so-called purge), in order to prevent inert components accumulating within the synthesis loop. This measure is also taught in the unexamined German Patent Application DE 2934332 A1 and in the European Patent Application EP 1016643 A1.

The purge gas stream discharged from the synthesis loop still is loaded with significant fractions of methanol. The same applies for other waste gas streams which are obtained within the methanol synthesis and the processing of the raw products, such as for example waste gases from methanol expansion tanks or waste gases from storage tanks for crude methanol, methanol-water mixtures or pure methanol.

Methanol storage tanks frequently are designed as fixed-roof tanks, wherein for inertization of the inner volume not filled with methanol the same frequently is rinsed or filled with nitrogen. The nitrogen atmosphere thereby is saturated with methanol. When loading the tanks or due to tank breathing, for example due to solar radiation, nitrogen loaded with methanol is discharged from the tank, in order to avoid an overpressure in the tank.

The methanol fractions of such waste gases are quite significant due to the low boiling point of the methanol of 65° C. at ambient pressure, as the waste gases generally are saturated with methanol vapor at the respective temperature. For example, under saturation conditions the methanol concentration in a waste gas stream with a temperature of 42° C. roughly is 33 vol-%.

In view of these methanol contents it is plausible that the recovery of the methanol from the waste gases provides an important contribution to the economy of the methanol synthesis process. Against the background of the high toxicity of the methanol, on the other hand, it is not justifiable either for reasons of environmental protection to emit waste gases with such high methanol contents to the environment without aftertreatment. Finally, high methanol contents in waste gases also create problems during their further processing, as methanol can condense out and thus for example damage gas burners.

Due to the high water solubility of the methanol, washing of the waste gases with water as washing agent has proved its worth as separation method. The disclosed European Patent Application EP 2 168 938 A1 for example teaches the recovery of methanol from waste gases of the crude methanol distillation by water washing in a countercurrent column. The European patent specification EP 0 802 893 B1 also describes the separation and recovery of methanol from waste gases of the crude methanol distillation by water washing.

The U.S. Pat. No. 5,346,593 A describes a distillation column for obtaining crude methanol, which at its head is equipped with a water washing stage and serves for the separation of methanol residues from a waste gas stream leaving the column.

Finally, the European patent specification EP 0 009 385 B1 discloses the separation of methanol from the purge gas stream discharged from the synthesis cycle by means of water washing and the recovery of the separated methanol by means of distillation.

In sum, however, it is to be noted that despite the prior art discussed above there still exists a need for optimized processes and apparatuses for the separation and recovery of methanol from various waste gas streams which are obtained within the methanol synthesis and the processing of the raw products. In particular with regard to the integration of such process stages into the complex flow chart of the processing of the crude methanol, the recovery of methanol from several of said waste gas types and with regard to the procedural design of the apparatuses used there still is a need for optimization.

SUMMARY OF THE INVENTION

Against this background it is the object of the present invention to provide a process and an apparatus in which or by which an efficient recovery of methanol from process waste gases of the synthesis and further processing of methanol is ensured.

This object is solved by a process with the features of claim 1 and by an apparatus with the features of claim 10. Further aspects of the invention will be found in the respective sub-claims.

PROCESS ACCORDING TO AN EMBODIMENT OF THE INVENTION

A process for the recovery of methanol from process waste gases of the methanol synthesis, comprising the following process steps:
(a) converting a synthesis gas stream under methanol synthesis conditions in at least one methanol synthesis reactor which is arranged in a synthesis gas circuit for non-converted synthesis gas,
(b) discharging a liquid crude methanol stream from the synthesis gas circuit and discharging a purge gas stream from the synthesis gas circuit, wherein the purge gas stream is loaded with methanol vapor, (c) introducing the purge gas stream into a purge gas washing apparatus, contacting the purge gas stream in the purge gas washing apparatus with a water stream as washing agent which is guided through the purge gas washing apparatus in counterflow to the purge gas stream, wherein the water stream absorbs at least a part of the methanol from the purge gas stream, (d) discharging a water stream loaded with methanol and a purge gas stream depleted of methanol from the purge gas washing apparatus, (e) introducing the liquid crude methanol stream into an expansion tank in which the pressure of the liquid crude methanol stream is reduced, wherein an expansion gas stream loaded with methanol and a depressurized crude methanol stream are obtained, (f) introducing the expansion gas stream into an expansion gas washing apparatus, contacting the expansion gas stream in the expansion gas washing apparatus with a water stream as washing agent which is guided through the expansion gas washing apparatus in counterflow to the expansion gas stream, wherein the water stream absorbs at least a part of the methanol from the expansion gas stream, (g) discharging a water stream loaded with methanol and an expansion gas stream depleted of methanol from the expansion gas washing apparatus, wherein the water stream loaded with methanol is added to the depressurized crude methanol stream, (h) introducing the depressurized crude methanol stream into a storage tank in which it is stored until its further processing or further use and in the process is covered by an inertizing gas which thereby is loaded with methanol, (i) discharging an inertizing gas stream loaded with methanol from the storage tank and introducing said gas stream into an inertizing gas washing apparatus, contacting the inertizing gas stream in the inertizing gas washing apparatus with a water stream as washing agent which is guided through the inertizing gas washing apparatus in counterflow to the inertizing gas stream, wherein the water stream absorbs at least a part of the methanol from the inertizing gas stream, (j) discharging a water stream loaded with methanol and an inertizing gas stream depleted of methanol from the inertizing gas washing apparatus.

Apparatus According to an Embodiment of the Invention

An apparatus for the recovery of methanol from process waste gases of the methanol synthesis, comprising the following components and assemblies:

(a) a methanol synthesis reactor which is arranged in a synthesis gas circuit for non-converted synthesis gas, (b) a conduit for discharging a liquid crude methanol stream from the synthesis gas circuit and a conduit for discharging a purge gas stream from the synthesis gas circuit, wherein the purge gas stream is loaded with methanol vapor, (c) a purge gas washing apparatus designed as countercurrent washer, a conduit for introducing the purge gas stream into a purge gas washing apparatus, a conduit for supplying a water stream as washing agent, a conduit for discharging a water stream loaded with methanol, and a conduit for discharging a purge gas stream depleted of methanol from the purge gas washing apparatus, (d) an expansion tank in which the pressure of the liquid crude methanol stream is reduced, a conduit for introducing the liquid crude methanol stream into the expansion tank, an expansion gas washing apparatus designed as countercurrent washer which is connected with the expansion tank, a conduit for introducing a water stream as washing agent into the expansion gas washing apparatus, a conduit for discharging a depressurized crude methanol stream, and a conduit for discharging an expansion gas stream depleted of methanol, (e) a storage tank, a conduit for introducing the depressurized crude methanol stream into the storage tank, a conduit for introducing an inertizing gas and a conduit for discharging an inertizing gas stream loaded with methanol from the storage tank, a conduit for discharging the crude methanol, (f) an inertizing gas washing apparatus designed as countercurrent washer, a conduit for introducing an inertizing gas stream loaded with methanol into the inertizing gas washing apparatus, a conduit for introducing a water stream as washing agent into the inertizing gas washing apparatus, a conduit for discharging an inertizing gas stream depleted of methanol, and a conduit for discharging a water stream loaded with methanol from the inertizing gas washing apparatus.

The methanol synthesis conditions required for the conversion of synthesis gas to methanol are known to the skilled person from the prior art, for example from the documents discussed above. This in particular, but not exclusively, relates to process conditions such as temperatures, pressures, suitable space velocities and catalysts to be used. Necessary adaptations of these conditions to the respective operating requirements will be made on the basis of routine experiments.

Purge gas or alternatively flushing gas is understood to be a gas fraction withdrawn from a system, for example from the synthesis gas circuit of the methanol synthesis, which mostly is small as compared to the gas inventory present in the system. The withdrawal of the purge gas prevents the steady increase of the gas inventory of the system and serves the discharge of impurities, by-products and/or inert components.

Crude methanol is understood to be the primary product originating directly from the methanol synthesis before being processed to pure methanol by distillation. However, first processing or conditioning steps can be carried out already with the crude methanol.

The water used as washing agent mostly is demineralized water. However, other water qualities, in particular those of higher purity, for example high-purity water or distilled water, can also be used as washing agent. Water of lower purity can be used as washing agent when the accompanying substances present create no problems in downstream process stages and the product specifications of the pure methanol product are complied with.

Preferred Aspects of the Invention

In a preferred aspect of the process according to the invention the purge gas stream depleted of methanol, which is obtained in step (d), is supplied to a hydrogen recovery apparatus. As hydrogen recovery apparatus for example a pressure swing adsorption plant (PSA) or a membrane plant can be used. In this way, valuable hydrogen can be recovered from the purge gas stream and be recirculated to the methanol synthesis.

In a further aspect of the process according to the invention the water stream loaded with methanol, which is obtained in step (d), is at least partly supplied to the expansion tank. In this way, the water stream loaded with methanol can be supplied to the further processing together with other water streams containing methanol, so that no separate processing apparatuses are required for the water stream loaded with methanol, which is obtained in step (d).

In a further preferred aspect of the process according to the invention the water stream loaded with methanol, which is obtained in step (d), is at least partly used as washing agent in the expansion gas washing apparatus. It here is advantageous that the demineralized water mostly used as washing agent is saved in part or completely, whereby the costs for its provision are reduced.

It furthermore is advantageous when at least a part of the depressurized crude methanol stream obtained in process step (e) is supplied to a distillation apparatus without intermediate storage in the storage tank. Storage capacities for crude methanol thereby can be saved and the corresponding storage tanks can be designed smaller.

In a particular aspect of the invention it is possible to introduce at least a part of the expansion gas stream depleted of methanol, which is obtained in process step (g), into the storage tank as inertizing gas. With this aspect of the invention it is possible to wholly or partly save inertizing gases such as for example nitrogen.

It also is favorable when at least a part of the water stream loaded with methanol, which is obtained in process step (j), is used as washing agent in the expansion gas washing apparatus. It here is advantageous that the demineralized water mostly used as washing agent is saved in part or completely, whereby the costs for its provision are reduced.

It furthermore was found to be advantageous when at least a part of the water stream loaded with methanol, which is obtained in process step (j), is supplied to the expansion tank. In this way, the water stream loaded with methanol can be supplied to the further processing together with other water streams containing methanol, so that no separate processing apparatuses are required for the water stream loaded with methanol, which is obtained in step (d).

Particularly preferably, the process according to the invention is used for the recovery of methanol from process waste gases of a plant for the synthesis of methanol, in which methanol is produced from coal-based synthesis gas. Due to the C/H ratio in the feedstock coal, coal-based synthesis gas in particular is characterized by a high content of carbon monoxide, but a relatively low water content. A defined water content which is increased with respect to the original content in the coal-based synthesis gas, however, is quite desirable. It provides certain advantages when processing the crude methanol by distillation, as in this way undesired non-polar impurities, for example alkanes obtained as by-products of the methanol synthesis, can be separated from the methanol more easily. Charging the crude methanol with water as washing agent therefore is quite advantageous at various points of the process.

In a particular design of the apparatus according to the invention the same furthermore comprises a hydrogen recovery apparatus and a conduit for introducing a purge gas stream depleted of methanol into the hydrogen recovery apparatus. As hydrogen recovery apparatus for example a pressure swing adsorption plant (PSA) or a membrane plant can be used. In this way, valuable hydrogen can be recovered from the purge gas stream and be recirculated to the methanol synthesis.

Preferably, the apparatus according to the invention furthermore comprises a conduit for supplying the water stream loaded with methanol, which is obtained in process step (d), to the expansion tank. In this way, the water stream loaded with methanol can be supplied to the further processing together with other water streams containing methanol, so that no separate processing apparatuses are required for the water stream loaded with methanol, which is obtained in step (d).

In a further aspect, the apparatus according to the invention furthermore comprises a conduit for supplying the water stream loaded with methanol, which is obtained in process step (d), to the expansion gas washing apparatus as washing agent. It here is advantageous that the demineralized water mostly used as washing agent is saved in part or completely, whereby the costs for its provision are reduced.

Favorably, the apparatus according to the invention furthermore comprises a distillation apparatus and a conduit for supplying the depressurized crude methanol stream obtained in process step (e) to the distillation apparatus. Storage capacities for crude methanol thereby can be saved and the corresponding storage tanks can be designed smaller.

In a further aspect, the apparatus according to the invention furthermore comprises a conduit for supplying at least a part of the expansion gas stream depleted of methanol, which is obtained in process step (g), into the storage tank as inertizing gas. With this aspect of the invention it is possible to wholly or partly save inertizing gases such as for example nitrogen.

It is favorable when the apparatus according to the invention furthermore comprises a conduit for supplying at least a part of the water stream loaded with methanol, which is obtained in process step (j), to the expansion gas washing apparatus as washing agent. It here is advantageous that the demineralized water mostly used as washing agent is saved in part or completely, whereby the costs for its provision are reduced.

Preferably, the apparatus according to the invention furthermore comprises a conduit for supplying at least a part of the water stream loaded with methanol, which is obtained in process step (j), to the expansion tank. In this way, the water stream loaded with methanol can be supplied to the further processing together with other water streams containing methanol, so that no separate processing apparatuses are required for the water stream loaded with methanol, which is obtained in step (d).

Particularly preferably, the apparatus according to the invention is located in a plant for the production of methanol by conversion of coal-based synthesis gas. Due to the C/H ratio in the feedstock coal, coal-based synthesis gas in particular is characterized by a high content of carbon monoxide, but a relatively low water content. A defined water content which is increased with respect to the original content in the coal-based synthesis gas, however, is quite desirable. It provides certain advantages when processing the crude methanol by distillation, as in this way undesired non-polar impurities, for example alkanes obtained as by-products of the methanol synthesis, can be separated from the methanol more easily.

Charging the crude methanol with water as washing agent therefore is quite advantageous at various points of the process.

BRIEF DESCRIPTION OF THE DRAWINGS

Further features, advantages and possible applications of the invention can also be taken from the following description of exemplary embodiments and numerical examples as well as the drawings. All features described and/or illustrated form the subject-matter of the invention per se or in any combination, independent of their inclusion in the claims or their back-reference.

In the drawings.

DETAILED DESCRIPTION OF THE INVENTION

Figure 1:
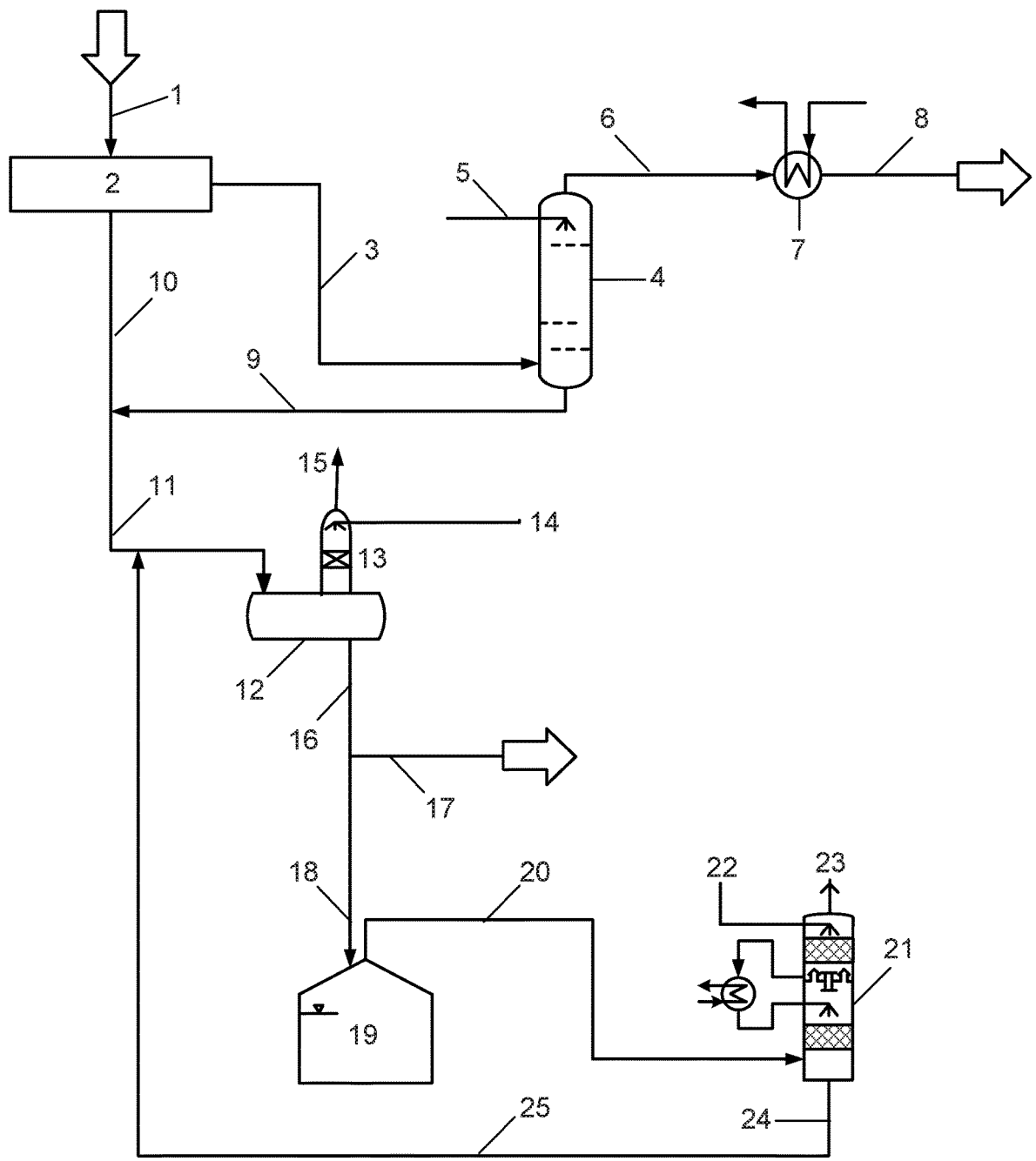
FIG. 1 shows the schematic representation of the process according to the invention and the apparatus according to the invention in a first aspect.

The process of the invention and the apparatus of the invention according to a first aspect are explained in FIG. 1. Via conduit 1 synthesis gas consisting of hydrogen and carbon oxides is introduced into the methanol synthesis reactor 2 arranged in a synthesis gas circuit, which here is shown only schematically and is not explained in detail, in which the synthesis gas is partly converted to methanol under the conditions of methanol synthesis. The crude methanol produced in the process is discharged from the methanol synthesis reactor via conduit 10.

The largest part of the synthesis gas not converted during the methanol synthesis is recirculated to the inlet of the methanol synthesis reactor via the non-illustrated synthesis gas circuit. Via conduit 3, the remaining fraction of the non-converted synthesis gas is discharged from the methanol synthesis reactor as purge gas or flushing gas and guided to the purge gas washing apparatus 4. This is a washing column known per se, which can be equipped with trays, packed beds or structured packings, in order to intensify the mass transfer between gas and liquid. The purge gas stream is charged to the purge gas washing apparatus at its bottom side and is countercurrently brought in contact with a water stream supplied as washing agent via conduit 5, whereby its content of methanol vapor is reduced. In the present exemplary embodiment and in those described below, demineralized water is used as washing agent—unless otherwise noted.

The purge gas depleted of methanol leaves the purge gas washing apparatus via conduit 6. It can then optionally be heated in the heat exchanger 7 by indirect heat exchange against low-pressure steam as heating medium and via conduit 8 be discharged from the process and be guided to a non-illustrated hydrogen recovery system.

The water loaded with methanol in the purge gas washing apparatus is discharged from the same via conduit 9 and together with the crude methanol supplied via conduit 10 guided to the expansion tank 12 via conduit 11. The mixture of crude methanol and water is depressurized in said expansion tank from 7.0 MPa,g to a pressure of 0.5 MPa,g (,g designates the corresponding pressure unit at overpressure). In the expansion gas washing apparatus 13 constructionally connected with the expansion tank and in fluid connection with the same the gases or vapors released during the depressurization are brought in contact with a water stream supplied as washing agent via conduit 14, whereby its content of methanol vapor is reduced. The expansion gas washing apparatus also is a washing column known per se, which can be equipped with trays, packed beds or structured packings, in order to intensify the mass transfer between gas and liquid. The expansion gas stream depleted of methanol leaves the expansion gas washing apparatus via conduit 15.

The depressurized mixture of crude methanol and water is discharged from the expansion tank 12 via conduit 16. Via conduit 17 it can completely or partly be guided to a non-illustrated distillation apparatus in which the crude methanol is processed further to pure methanol by distillative separation of water.

Via conduit 18, the fraction of the mixture of crude methanol and water not guided to the distillation apparatus is guided to the tank 19 and introduced into the same. At a later time, crude methanol can be withdrawn from the tank and be supplied to the distillative processing. Supply and discharge conduits for crude methanol are not shown in the drawing. The tank 19 is a fixed-roof tank in which the free inner volume of the tank is filled by nitrogen, which is supplied via a non-illustrated conduit, and thus is inertized. The nitrogen atmosphere thereby is saturated with methanol. When loading the tanks or due to tank breathing, for example due to solar radiation, nitrogen loaded with methanol is discharged from the tank via conduit 20, in order to avoid an overpressure in the tank. This inertizing gas stream loaded with methanol vapor is guided to the inertizing gas washing apparatus 21, charged to the same on its bottom side, and is countercurrently brought in contact with a water stream supplied as washing agent via conduit 22, whereby its content of methanol vapor is reduced.

The inertizing gas washing apparatus also is designed as washing column and equipped with trays, packed beds or structured packings, in order to intensify the mass transfer between gas and liquid. It is, however, separated into an upper and a lower part by a separation tray arranged approximately in the middle of the column, which is designed as chimney tray. The washing agent partly loaded with methanol accumulates on the same, as due to the design as chimney tray it cannot get into the lower column part within the column, whereas the inertizing gas stream to be purified freely can flow from the lower into the upper column part. The washing agent partly loaded with methanol, on the other hand, is guided out of the column via a conduit, cooled in an intermediate cooler and again charged to the column at the upper end of the lower column part. Due to cooling of the partly loaded washing agent, its absorption capacity for further methanol is increased.

Via conduit 24, the washing agent loaded with methanol is discharged from the inertizing gas washing apparatus and via conduits 25 and 11 guided to the expansion tank 12. If distinctly different pressures exist in the conduits 25 and 11, the washing agent loaded with methanol also can be guided to the expansion tank separate from conduit 11 and/or an expansion valve is provided in the junction of conduit 25 and conduit 11.

Figure 2:
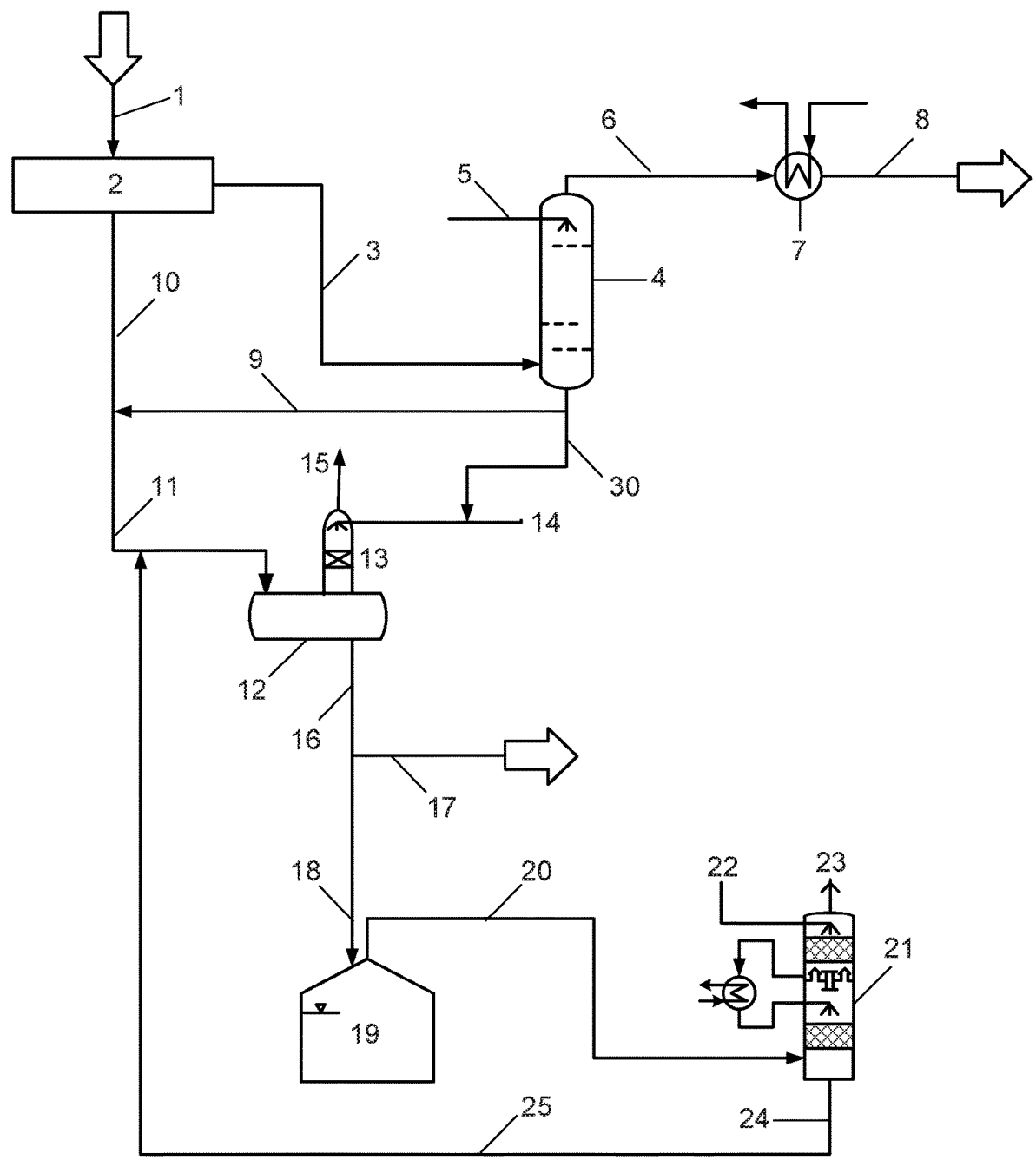
FIG. 2 shows the schematic representation of the process according to the invention and the apparatus according to the invention in a second aspect.

FIG. 2 schematically illustrates the procedure of the process according to the invention and the construction of an apparatus according to the invention in a second aspect. The process according to the invention and the apparatus according to the invention correspond to the aspect shown in FIG. 1 up to the plant component 25. Now, however, a conduit 30 is added, with which the water stream loaded with methanol, which is discharged from the purge gas washing apparatus, is at least partly supplied to the expansion gas washing apparatus and finally to the expansion tank. In this way, the water stream loaded with methanol can be supplied to the further processing together with other water streams containing methanol, so that no separate processing apparatuses are required for the water stream loaded with methanol, which is obtained in the purge gas washing apparatus. In addition, the water stream loaded with methanol can replace at least a part of the demineralized water used as washing agent.

Figure 3:
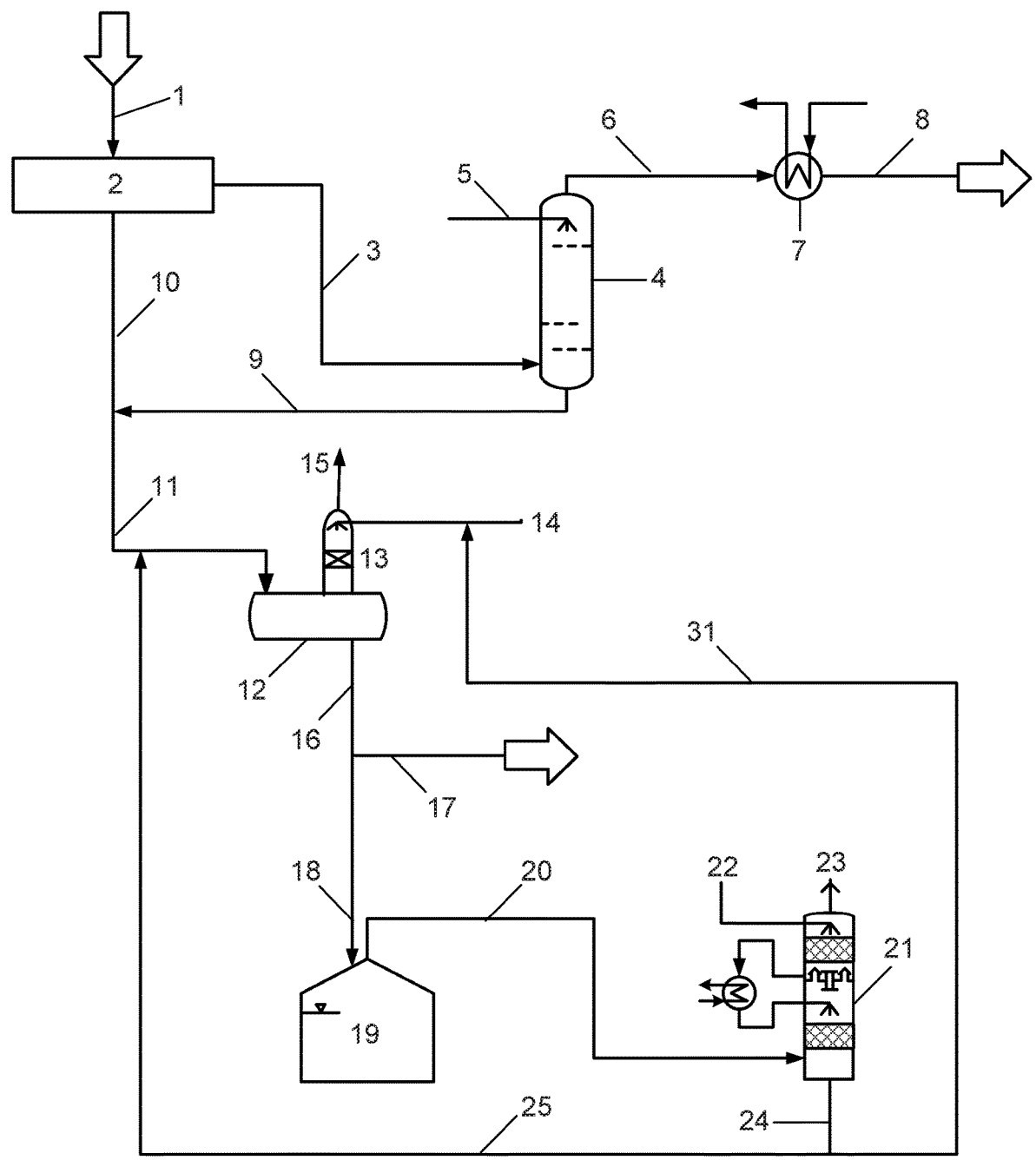
FIG. 3 shows the schematic representation of the process according to the invention and the apparatus according to the invention in a third aspect.

FIG. 3 schematically illustrates the procedure of the process according to the invention and the construction of an apparatus according to the invention in a third aspect. The process according to the invention and the apparatus according to the invention correspond to the aspect shown in FIG. 1 up to the plant component 25. Now, however, a conduit 31 is added, with which the water stream loaded with methanol, which is discharged from the inertizing gas washing apparatus, is at least partly supplied to the expansion gas washing apparatus and finally to the expansion tank. In this way, the water stream loaded with methanol can be supplied to the further processing together with other water streams containing methanol, so that no separate processing apparatuses are required for the water stream loaded with methanol, which is obtained in the inertizing gas washing apparatus. In addition, the water stream loaded with methanol can replace at least a part of the demineralized water used as washing agent.

Figure 4:
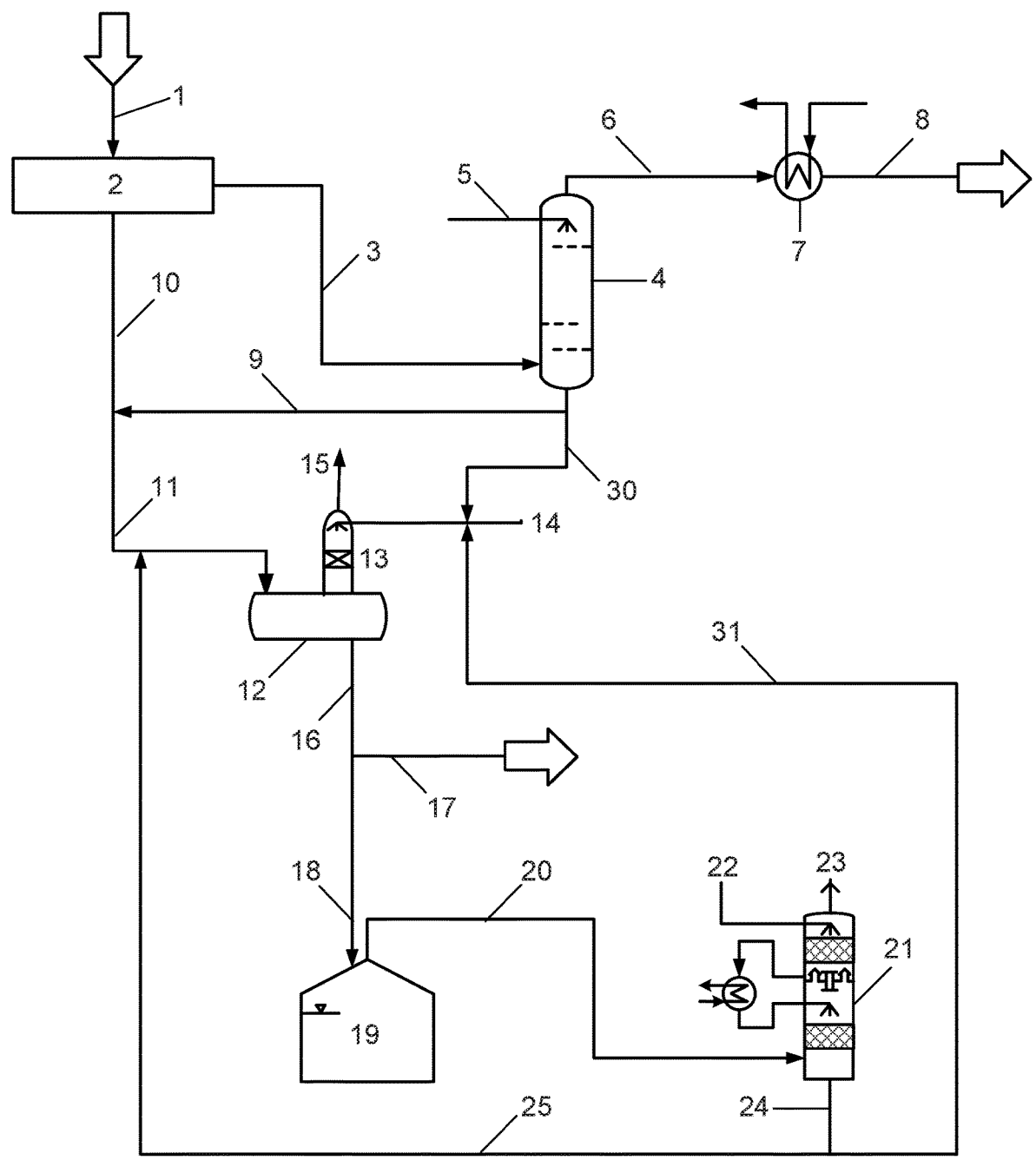
FIG. 4 shows the schematic representation of the process according to the invention and the apparatus according to the invention in a fourth aspect.

FIG. 4 schematically illustrates the procedure of the process according to the invention and the construction of an apparatus according to the invention in a fourth aspect. The process according to the invention and the apparatus according to the invention correspond to the aspect shown in FIG. 1 up to the plant component 25. Now, however, both conduit 30 and conduit 31 are added, whose function has been shown in the aspects illustrated in FIG. 2 and FIG. 3 and discussed above in connection with the same. Due to the design as shown in FIG. 4, a particularly large fraction of the demineralized water used as washing agent can be replaced by water streams loaded with methanol from the purge gas washing apparatus and the inertizing gas washing apparatus.

NUMERICAL EXAMPLES

In the following Tables numerical examples are listed for the inventive purification of purge gas (Table 1), of expansion gas (Table 2) and of tank waste gas (inertizing gas) (Table 3). Furthermore, Tables 4 and 5 show the purification of expansion gas according to particular aspects of the invention, in which partly loaded waste water from the purge gas washing apparatus (Table 4, conduit 30) or from the inertizing gas washing apparatus (Table 5, conduit 31) is recirculated to the expansion gas washing apparatus and used there as washing agent.

TABLE 1

| Purge gas purification | | | | |
|---|---|---|---|---|
| | Purge gas | Demin. water | Purge gas purified | Waste water |
| Mole fraction | | | | |
| $CH_3OH$ | 0.0057 | 0.0000 | 0.0000 | 0.0461 |
| $H_2O$ | 0.0001 | 1.0000 | 0.0015 | 0.9515 |
| $CO_2$ | 0.0424 | 0.0000 | 0.0424 | 0.0013 |
| CO | 0.0643 | 0.0000 | 0.0646 | 0.0001 |
| $H_2$ | 0.7990 | 0.0000 | 0.8026 | 0.0009 |
| AR | 0.0000 | 0.0000 | 0.0000 | 0.0000 |
| $N_2$ | 0.0883 | 0.0000 | 0.0887 | 0.0001 |
| $CH_4$ | 0.0002 | 0.0000 | 0.0002 | 0.0000 |

TABLE 1-continued

| Purge gas purification | | | | |
|---|---|---|---|---|
| | Purge gas | Demin. water | Purge gas purified | Waste water |
| Total stream kmol/h | 1288.1 | 152.9 | 1282.1 | 158.9 |
| Total stream kg/h | 10223.7 | 2754.9 | 10010.3 | 2968.3 |
| Temperature °C. | 40.0 | 42.2 | 43.9 | 44.7 |
| Pressure MPag | 7.0 | 8.1 | 7.0 | 7.0 |

TABLE 2

| Expansion gas purification | | | |
|---|---|---|---|
| | Expansion gas | Demin. water | Expansion gas purified |
| Mole fraction | | | |
| $CH_3OH$ | 0.0579 | 0.0000 | 0.0000 |
| $H_2O$ | 0.0018 | 1.0000 | 0.0132 |
| $CO_2$ | 0.2285 | 0.0000 | 0.2392 |
| CO | 0.0397 | 0.0000 | 0.0417 |
| $H_2$ | 0.3607 | 0.0000 | 0.3789 |
| AR | 0.0379 | 0.0000 | 0.0398 |
| $N_2$ | 0.2676 | 0.0000 | 0.2812 |
| $CH_4$ | 0.0058 | 0.0000 | 0.0061 |
| Total stream kmol/h | 177.9 | 277.5 | 169.3 |
| Total stream kg/h | 4072.5 | 5000.0 | 3769.8 |
| Temperature °C. | 40.6 | 40.0 | 40.4 |
| Pressure MPag | 0.5 | 0.5 | 0.5 |

TABLE 3

| Inertizing gas purification | | | | |
|---|---|---|---|---|
| | Inertizing gas | Demin. water | Inertizing gas purified | Waste water |
| Mole fraction | | | | |
| $CH_3OH$ | 0.3338 | 0.0000 | 0.0043 | 0.2671 |
| $H_2O$ | 0.0000 | 1.0000 | 0.1425 | 0.7328 |
| $CO_2$ | 0.0000 | 0.0000 | 0.0000 | 0.0000 |
| CO | 0.0000 | 0.0000 | 0.0000 | 0.0000 |
| $H_2$ | 0.0000 | 0.0000 | 0.0000 | 0.0000 |
| AR | 0.0000 | 0.0000 | 0.0000 | 0.0000 |
| $N_2$ | 0.6662 | 0.0000 | 0.8532 | 0.0000 |
| $CH_4$ | 0.0000 | 0.0000 | 0.0000 | 0.0000 |
| Total stream kmol/h | 180.0 | 183.2 | 140.5 | 222.6 |
| Total stream kg/h | 5284.5 | 3300.0 | 3739.2 | 4845.3 |
| Temperature °C. | 40.3 | 40.0 | 53.1 | 50.2 |
| Pressure MPag | 0.0 | 0.4 | 0.0 | 0.5 |

TABLE 4

Expansion gas purification with conduit (30)

|  | Expansion gas | Waste water | Expansion gas purified |
|---|---|---|---|
| Mole fraction | | | |
| CH3OH | 0.0575 | 0.0461 | 0.0082 |
| $H_2O$ | 0.0012 | 0.9515 | 0.0202 |
| CO2 | 0.2264 | 0.0013 | 0.2339 |
| CO | 0.0399 | 0.0001 | 0.0412 |
| H2 | 0.3625 | 0.0009 | 0.3745 |
| AR | 0.0380 | 0.0000 | 0.0392 |
| N2 | 0.2686 | 0.0001 | 0.2769 |
| CH4 | 0.0058 | 0.0000 | 0.0060 |
| Total stream kmol/h | 176.9 | 158.9 | 171.7 |
| Total stream kg/h | 4036.8 | 2968.3 | 3819.4 |
| Temperature ° C. | 39.9 | 44.6 | 49.6 |
| Pressure MPag | 0.5 | 0.5 | 0.5 |

TABLE 5

Expansion gas purification with conduit (31)

|  | Expansion gas | Waste water | Expansion gas purified |
|---|---|---|---|
| Mole fraction | | | |
| CH3OH | 0.0571 | 0.2671 | 0.0344 |
| $H_2O$ | 0.0012 | 0.7328 | 0.0165 |
| CO2 | 0.2259 | 0.0000 | 0.2263 |
| CO | 0.0399 | 0.0000 | 0.0403 |
| H2 | 0.3630 | 0.0000 | 0.3666 |
| AR | 0.0380 | 0.0000 | 0.0384 |
| N2 | 0.2690 | 0.0000 | 0.2716 |
| CH4 | 0.0058 | 0.0000 | 0.0058 |
| Total stream kmol/h | 176.7 | 222.6 | 174.9 |
| Total stream kg/h | 4027.1 | 4845.3 | 3929.7 |
| Temperature ° C. | 39.7 | 50.0 | 49.7 |
| Pressure MPag | 0.5 | 0.5 | 0.5 |

INDUSTRIAL APPLICABILITY

With the invention, an efficient recovery of methanol from waste gases loaded with methanol is proposed in an integrated flow chart for the production and processing of methanol. The methanol fractions separated from the waste gases are recovered within the already existing, distillative processing of the crude methanol to pure methanol, so that no separate apparatuses for the recovery of the methanol from the loaded scrubber waste waters are required. The valuable substance methanol is recovered and the impact on the environment is reduced. By means of particular aspects of the invention the need for water as washing agent can be reduced further.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 1 conduit
2 methanol synthesis reactor
3 conduit
4 purge gas washing apparatus
5 conduit
6 conduit
7 heat exchanger
8 conduit
9 conduit
10 conduit
11 conduit
12 expansion tank
13 expansion gas washing apparatus
14 conduit
15 conduit
16 conduit
17 conduit
18 conduit
19 tank
20 conduit
21 inertizing gas washing apparatus
22 conduit
23 conduit
24 conduit
25 conduit
30 conduit
31 conduit

The invention claimed is:

1. A process for the recovery of methanol from process waste gases of the methanol synthesis, comprising the following process steps:
   a) converting a synthesis gas stream under methanol synthesis conditions in at least one methanol synthesis reactor which is arranged in a synthesis gas circuit for non-converted synthesis gas;
   b) discharging a liquid crude methanol stream from the synthesis gas circuit and discharging a purge gas stream from the synthesis gas circuit, wherein the purge gas stream is loaded with methanol vapor;
   c) introducing the purge gas stream into a purge gas washing apparatus, contacting the purge gas stream in the purge gas washing apparatus with a water stream as washing agent which is guided through the purge gas washing apparatus in counterflow to the purge gas stream, wherein the water stream absorbs at least a part of the methanol from the purge gas stream;
   d) discharging a water stream loaded with methanol and a purge gas stream depleted of methanol from the purge gas washing apparatus;
   e) introducing the liquid crude methanol stream into an expansion tank in which the pressure of the liquid crude methanol stream is reduced, wherein an expansion gas stream loaded with methanol and a depressurized crude methanol stream are obtained;
   f) introducing the expansion gas stream into an expansion gas washing apparatus, contacting the expansion gas stream in the expansion gas washing apparatus with a water stream as washing agent which is guided through the expansion gas washing apparatus in counterflow to the expansion gas stream, wherein the water stream absorbs at least a part of the methanol from the expansion gas stream;
   g) discharging a water stream loaded with methanol and an expansion gas stream depleted of methanol from the expansion gas washing apparatus, wherein the water stream loaded with methanol is added to the depressurized crude methanol stream;
   h) introducing the depressurized crude methanol stream into a storage tank in which it is stored until its further processing or further use and in the process is covered by an inertizing gas which thereby is loaded with methanol;
   i) discharging an inertizing gas stream loaded with methanol from the storage tank and introducing the same into an inertizing gas washing apparatus, contacting the inertizing gas stream in the inertizing gas washing apparatus with a water stream as washing agent which is guided through the inertizing gas washing apparatus in counterflow to the inertizing gas stream, wherein the water stream absorbs at least a part of the methanol from the inertizing gas stream; and
   j) discharging a water stream loaded with methanol and an inertizing gas stream depleted of methanol from the inertizing gas washing apparatus.

2. The process according to claim 1, wherein the purge gas stream depleted of methanol, which is obtained in step (d), is supplied to a hydrogen recovery apparatus.

3. The process according to claim 1, wherein the water stream loaded with methanol, which is obtained in step (d), is at least partly supplied to the expansion tank.

4. The process according to claim 1, wherein the water stream loaded with methanol, which is obtained in step (d), is at least partly used as washing agent in the expansion gas washing apparatus.

5. The process according to claim 1, wherein at least a part of the depressurized crude methanol stream obtained in process step (e) is supplied to a distillation apparatus without intermediate storage in the storage tank.

6. The process according to claim 1, wherein at least a part of the expansion gas stream depleted of methanol, which is obtained in step (g), is introduced into the storage tank as inertizing gas.

7. The process according to claim 1, wherein at least a part of the water stream loaded with methanol, which is obtained in step (j), is used as washing agent in the expansion gas washing apparatus.

8. The process according to claim 1, wherein at least a part of the water stream loaded with methanol, which is obtained in step (j), is supplied to the expansion tank.

9. An apparatus for the recovery of methanol from process waste gases of the methanol synthesis, the apparatus comprising:
   a) a methanol synthesis reactor which is arranged in a synthesis gas circuit for non-converted synthesis gas;
   b) a conduit for discharging a liquid crude methanol stream from the synthesis gas circuit and a conduit for discharging a purge gas stream from the synthesis gas circuit, wherein the purge gas stream is loaded with methanol vapor;
   c) a purge gas washing apparatus designed as countercurrent washer, a conduit for introducing the purge gas stream into a purge gas washing apparatus, a conduit for supplying a water stream as washing agent, a conduit for discharging a water stream loaded with methanol, and a conduit for discharging a purge gas stream depleted of methanol from the purge gas washing apparatus;
   d) an expansion tank in which the pressure of the liquid crude methanol stream is reduced, a conduit for introducing the liquid crude methanol stream into the expansion tank, an expansion gas washing apparatus designed as countercurrent scrubber which is connected with the expansion tank, a conduit for introducing a water stream as washing agent into the expansion gas washing apparatus, a conduit for discharging a depressurized crude methanol stream, and a conduit for discharging an expansion gas stream depleted of methanol;
   e) a storage tank, a conduit for introducing the depressurized crude methanol stream into the storage tank, a conduit for introducing an inertizing gas and a conduit for discharging an inertizing gas stream loaded with methanol from the storage tank, a conduit for discharging the crude methanol; and
   f) an inertizing gas washing apparatus designed as countercurrent scrubber, a conduit for introducing an inertizing gas stream loaded with methanol into the inertizing gas washing apparatus, a conduit for introducing a water stream as washing agent into the inertizing gas washing apparatus, a conduit for discharging an inertizing gas stream depleted of methanol, and a conduit for discharging a water stream loaded with methanol from the inertizing gas washing apparatus.

10. The apparatus according to claim 9, furthermore comprising a hydrogen recovery apparatus and a conduit for introducing a purge gas stream depleted of methanol into the hydrogen recovery apparatus.

11. The apparatus according to claim 9, furthermore comprising a conduit for supplying the water stream loaded with methanol, which is obtained in process step (d), to the expansion tank.

12. The apparatus according to claim 9, furthermore comprising a conduit for supplying the water stream loaded with methanol, which is obtained in process step (d), to the expansion gas washing apparatus as washing agent.

13. The apparatus according to claim 9, furthermore comprising a distillation apparatus and a conduit for supplying the depressurized crude methanol stream obtained in process step (e) to the distillation apparatus.

14. The apparatus according to claim 9, furthermore comprising a conduit for supplying at least a part of the expansion gas stream depleted of methanol, which is obtained in process step (g), into the storage tank as inertizing gas.

15. The apparatus according to claim 9, furthermore comprising a conduit for supplying at least a part of the water stream loaded with methanol, which is obtained in process step (j), to the expansion gas washing apparatus as washing agent.

16. The apparatus according to claim 9, furthermore comprising a conduit for supplying at least a part of the water stream loaded with methanol, which is obtained in process step (j), to the expansion tank.

17. A plant configured for the production of methanol by conversion of coal=based synthesis gas comprising the apparatus as claimed in claim 9.

\* \* \* \* \*